US008366899B2

(12) United States Patent
Albrecht et al.

(10) Patent No.: US 8,366,899 B2
(45) Date of Patent: Feb. 5, 2013

(54) ISOELECTRIC FOCUSING SYSTEMS AND METHODS

(75) Inventors: Jacob Albrecht, New Brunswick, NJ (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 285 days.

(21) Appl. No.: 12/666,113

(22) PCT Filed: Jun. 20, 2008

(86) PCT No.: PCT/US2008/007743
§ 371 (c)(1),
(2), (4) Date: Nov. 15, 2010

(87) PCT Pub. No.: WO2009/002459
PCT Pub. Date: Dec. 31, 2008

(65) Prior Publication Data
US 2011/0062025 A1    Mar. 17, 2011

Related U.S. Application Data

(60) Provisional application No. 60/936,966, filed on Jun. 22, 2007.

(51) Int. Cl.
*G01N 27/447*    (2006.01)
*G01N 27/453*    (2006.01)
(52) U.S. Cl. ......... 204/548; 204/459; 204/610; 204/644
(58) Field of Classification Search .................. 204/548, 204/459, 610, 644
See application file for complete search history.

(56) References Cited

U.S. PATENT DOCUMENTS

| 3,412,007 | A | * | 11/1968 | Strickler ..................... 204/645 |
| 3,655,541 | A |   | 4/1972  | Strickler |
| 4,971,670 | A | * | 11/1990 | Faupel et al. ................ 204/459 |
| 5,439,571 | A | * | 8/1995  | Sammons et al. ............ 204/549 |
| 8,142,630 | B2| * | 3/2012  | Strand et al. ................. 204/451 |

FOREIGN PATENT DOCUMENTS

| EP | 0067549 A2 | 12/1982 |
| JP | 06-130035 A * | 5/1994 |
| WO | WO 2007/008064 A2 | 1/2007 |

OTHER PUBLICATIONS

JPO computer genertaed Englsih language translation of Hiroaki Matsumoto JP 06-130035 A, downloaded Sep. 22, 2012.*
Albrecht et al., "Micro free-flow IEF enhanced by active cooling and functionalized gels," *Electrophoresis*, 2006, 27, 4960-4969.

(Continued)

*Primary Examiner* — Alex Noguerola
(74) *Attorney, Agent, or Firm* — Wolf, Greenfield & Sacks, P.C.

(57) ABSTRACT

The present invention generally relates to devices and methods for the separation of species, including biological species. Some embodiments involve the use of free flow isoelectric focusing (FF-IEF) devices in the separation of a mixture of species. Various device configurations and/or features may enhance the performance of the devices, providing faster and more efficient devices and methods for separating mixtures of species with high resolution. In some embodiments, separation of a mixture of species may be achieved with high resolution and with short sample residence times. Such devices may provide simplified, inexpensive, and optionally disposable devices for the separation of chemical and biological species and may optionally be integrated with orthogonal separation techniques, such as SDS-PAGE or capillary electrophoresis.

37 Claims, 12 Drawing Sheets

OTHER PUBLICATIONS

Albrecht et al., "Multi-stage free-flow isoelectric focusing for enhanced separation speed and resolution," Abstract and Poster from 2006 Micro Total Analysis Systems Conference.

Albrecht et al., "Rapid free flow isoelectric focusing via novel electrode structures," 9th International Conference on Miniaturized Systems for Chemistry and Life Sciences, Oct. 9-13, 2005, Boston, Massachusetts, USA, 1537-1539.

Kohlheyer et al., "Free-flow zone electrophoresis and isoelectric focusing using a microfabricated glass device with ion permeable membranes," *Lab on a Chip*, 2006, 6, 374-380.

Lu et al., "A microfabricated device for subcellular organelle sorting," *Anal. Chem.*, 2004, 76, 5705-5712.

Macounová et al., "Concentration and separation of proteins in microfluidic channels on the basis of transverse IEF," *Anal. Chem.*, 2001, 73, 1627-1633.

Xu et al., "Sub-second isoelectric focusing in free flow using a microfluidic device," *Lab on a Chip*, 2003, 3, 224-227.

International Search Report and Written Opinion from International Patent Application Serial No. PCT/US2008/007743, filed Jun. 20, 2008, mailed Dec. 29, 2008.

* cited by examiner

ISOELECTRIC FOCUSING SYSTEMS AND METHODS

STATEMENT REGARDING FEDERALLY SPONSORED RESEARCH AND DEVELOPMENT

This invention was made with government support under Grant No. P 50GM68762 awarded by the National Institutes of Health. The government has certain rights in the invention.

RELATED APPLICATIONS

This application is a U.S. National Stage application based on International Application No. PCT/US2008/007743, filed Jun. 20, 2008, which claims priority under 35 U.S.C. § 119(e) to United States Provisional Application Ser. No. 60/936,966, filed Jun. 22, 2007, the contents of which are incorporated herein by reference in their entirety.

FIELD OF THE INVENTION

The present invention generally relates to devices and methods for the separation of species, including biological species.

BACKGROUND OF THE INVENTION

Free flow isoelectric focusing (FF-IEF) is a mode of electrophoresis that occurs in a pH gradient. FF-IEF can continuously separate and concentrate amphoteric molecules on the basis of their isoelectric point (pI). Generally, FF-IEF involves flowing a sample solution containing a mixture of species through a rectangular chamber and applying an electric field to establish a pH gradient across the width of the chamber. The species within the mixture may be separated across the width of the rectangular channel according to the interaction of the different species with the pH gradient.

FF-IEF has been employed on a preparative scale, wherein a typical chamber may have a channel width on the order of at least tens of centimeters. Generally, in such cases, the distance between electrodes on either side of the channel may reduce the effectiveness of the electric field in establishing the pH gradient, and the pH gradient must be artificially established by the introduction of pH buffers into the channel. Thus, while preparative FF-IEF systems can fractionate large volumes of liquid with high recovery, the resulting fractions may have a net dilution of species, even for highly purified fractions. On an analytic scale, microfabricated FF-IEF devices may establish stable pH gradient without the need for additional pH buffers since the distance between electrodes is reduced. Such devices have been shown to effectively separate and concentrate species, such as fluorescent dyes, proteins and organelles, but often with lower resolution when compared to preparative systems.

Accordingly, improved devices and methods are needed.

SUMMARY OF THE INVENTION

The present invention relates to devices for separating a mixture of species comprising a channel constructed and arranged to receive a fluid flow, the channel comprising substantially non-parallel sidewalls, wherein a first portion of the channel has a channel width that is less than the channel width of a second portion of the channel; and at least two electrodes positioned on opposing, external sides of the channel and arranged to form an electric field substantially perpendicular to the primary direction of fluid flow; wherein, upon application of an electric field, the device is capable of establishing a pH gradient in a gradient orientation that is perpendicular to the primary direction of fluid flow.

The present invention also relates to devices for separating a mixture of species comprising a first region comprising a first channel having a channel width, the channel constructed and arranged to receive a fluid flow, and at least two electrodes positioned on opposing, external sides of the first channel and arranged to form an electric field substantially perpendicular to the primary direction of fluid flow; and a second region comprising at least two channels fluidly connected to the first channel, the at least two channels constructed and arranged to receive fluid flow from the first channel, and at least two electrodes positioned on opposing, external sides of each of the at least two channels and arranged to form an electric field substantially perpendicular to the primary direction of fluid flow, wherein, upon application of an electric field, the device is capable of establishing a pH gradient in a gradient orientation that is perpendicular to the primary direction of fluid flow.

The present invention also provides methods for separating a mixture of species, comprising providing a device comprising at least one channel having a channel width and a fluid flowing through the channel, the channel comprising a first region and a second region, wherein the first region has a first pH gradient across the channel in a gradient orientation that is perpendicular to the primary direction of fluid flow and the second region has a second pH gradient across the channel in the gradient orientation, wherein the first pH gradient is different from the second pH gradient; exposing a fluid sample comprising a mixture of species to the first region such that the fluid sample is affected by the first pH gradient; and exposing at least a portion of the fluid sample to the second region such that the fluid sample is affected by the second pH gradient, thereby separating the mixture of species.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to devices and methods for the separation of species, including biological species.

Specifically, the present invention involves the use of isoelectric focusing (IEF), including free flow isoelectric focusing (FF-IEF), in the separation of a mixture of species. The present invention provides various device configurations and/or features which may enhance the performance of the devices. For example, the present invention provides devices that can be faster and more efficient than other devices, and methods for separating mixtures of species with resolution that can be higher. A particular advantage of the present invention is that devices and methods described herein can achieve separation of a mixture of species with high resolution in a relatively short period of time, i.e., in a short sample residence time. The ability to quickly and effectively resolve or purify a mixture of species can reduce disadvantages associated with surface adsorption, joule heating, and device manufacturing costs. The invention thus provides simplified, inexpensive, and optionally disposable devices for the separation of chemical and biological species. Embodiments of the present invention may be integrated with or may compliment other separation techniques, such as SDS-PAGE or capillary electrophoresis.

Figure 1:
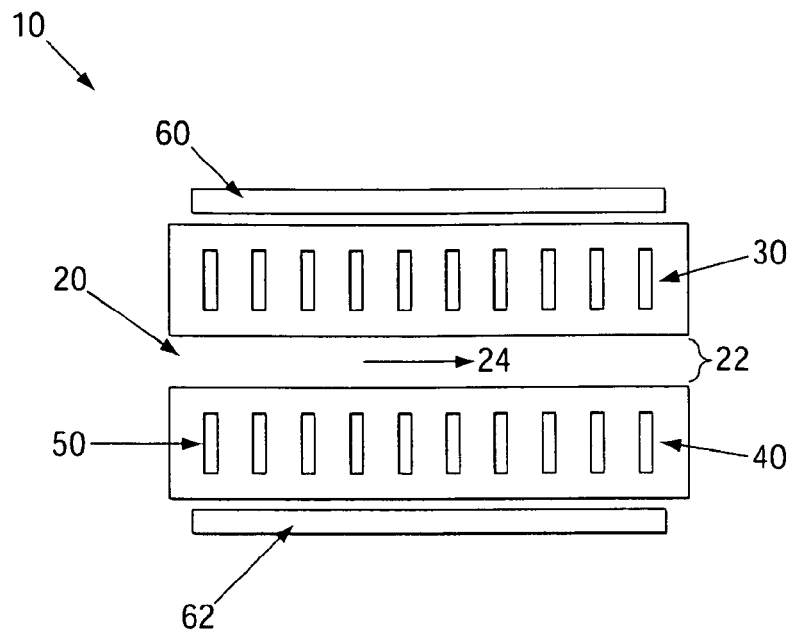
FIG. 1 show a schematic representation of a FF-IEF channel comprising an acidic, functionalized gel and a basic, functionalized gel on opposing sides of the channel.

Some embodiments of the invention involve the use of devices in which a mixture of species can be separated on the basis of the isoelectric points of individual species within the mixture. As used herein, "isoelectric point" is given its ordinary meaning in the art and refers to the pH at which a species is immobilized in an electric field. That is, a pH gradient may be formed in the presence of an electric field such that, species within a mixture, when introduced into the environment comprising the pH gradient, may migrate to a location corresponding to its isoelectric point (pI) where the species has no net charge. Such methods may be useful in the separation of a mixture of proteins, for example. This principle, which is known generally in the art, is illustrated schematically with reference to FIG. 1. As shown in FIG. 1, device 10 may comprise a channel 20 and electrodes 60 and 62, which may be positioned relative to channel 20 such that, upon application of an electric field, a pH gradient may be established in a direction which is perpendicular to the primary direction of fluid flow. A mixture of proteins may be flowed into channel 20 in a direction 24, wherein the proteins are separated in the pH gradient on the basis of isoelectric point.

The present invention generally involves the discovery that certain variations in the configuration of a FF-IEF device can greatly enhance overall performance of the device. In some cases, the devices may involve variation of, for example, at least one dimension of the channel through which the mixture of species flows. The dimension may include the length, width, height, diameter, shape, and/or other characteristic of at least a portion of the channel. Some embodiments may include variation in the configuration of various components and/or regions of the device. In some cases, the devices may include a different pH gradient within different regions of the device. That is, a mixture flowing through a device may be exposed to at least two or more different pH gradients in succession. The pH gradients may be different with respect to the range of pH units and/or the rate of change of pH units per millimeter of the channel (e.g., along the direction of the pH gradient). For example, a fluid sample flowing through the device may pass through a first region, wherein the fluid sample is exposed to a pH gradient spanning a large number of pH units, and, subsequently, may pass through a second region, wherein the fluid sample, or a portion thereof, is exposed to a pH gradient spanning a small number of pH units.

An electric field may be applied to at least a portion of the channel to establish the pH gradient in a gradient orientation that is essentially perpendicular to the primary direction of fluid flow within the channel. Typically, the electrodes may be positioned on opposing sides of the channel to establish an electric field therebetween. The electrodes may be also placed on external sides of the channel such that the electrodes do not directly contact the fluid flowing through the channel. This may advantageously reduce or prevent the introduction of bubbles, impurities, or other electrolysis products into the channel.

In some cases, a fluid sample comprising a mixture of species may be exposed to an electric field and pH gradient in a first region of the channel, wherein various species of the mixture are separated according to their isoelectric point along a direction that is substantially perpendicular to the primary direction of fluid flow. That is, the mixture undergoes a first separation of species to produced a first, resolved fluid sample. The resolved fluid sample may be subsequently exposed to an electric field and pH gradient in a second region of the channel, which may be the same or different than that of the first region, wherein at least a portion of the resolved, fluid sample from the first region is further separated to produce a second, resolved fluid sample wherein the species have improved separation from each other, i.e., the fluid sample is more highly resolved. The exposure of the mixture to multiple regions within the channel, each region having a different ability to affect the position of individual species of the mixture within the channel, may allow for the separation of a mixture of species with greater resolution and, in some cases, with greater speed and efficiency.

Figure 2:
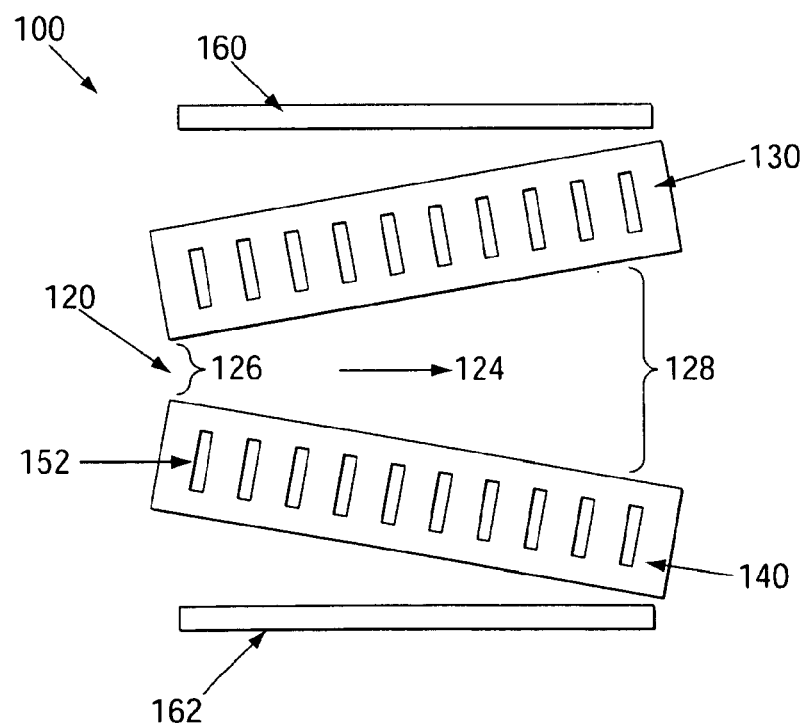
FIG. 2 show a schematic representation of a diverging channel design, according to one embodiment of the invention.

In some embodiments, the invention provides a device for separating a mixture of species, wherein the device comprises a channel design comprising substantially non-parallel sidewalls, i.e., a "diverging" channel design. The channel may comprise a first portion having a channel width that is less than the channel width of a second portion of the channel. For example, a fluid sample may be introduced into the channel have a narrow width, and, as the fluid sample flows through the channel, the width of the channel may increase. FIG. 2 shows an illustrative embodiment of a device comprising a diverging channel configuration of the invention. As shown in FIG. 2, device 100 comprises a channel 120 through which fluid may flow in a direction 124. The fluid may enter channel 120 and be exposed to a first region 126 having a relatively narrow channel width. The fluid may then flow further downstream and be exposed to a second region 128 having a relatively wide channel width. Region 126 and region 128 may each affect the fluid flowing through channel 120.

In some cases, the electric field applied to the channel in a first region of the channel may be substantially the same as that applied to the channel in the second region, for example, in a diverging channel configuration. That is, the electrodes may be separated by substantially the same distance and essentially the same voltage may be applied between electrodes at different regions of the channel. For example, two electrodes may be positioned on opposing sides of the channel in a parallel arrangement such that the distance between electrodes and the voltage applied between electrodes may be the same at any location in the channel between the two electrodes. As shown in FIG. 2, device 100 comprises electrodes 160 and 162 positioned parallel with respect to one another, forming an electric field in an orientation perpendicular to the primary direction of fluid flow within channel 120. As a result, the electric field in region 126 of the channel may be essentially the same as that in region 128 of the channel.

Figure 3:
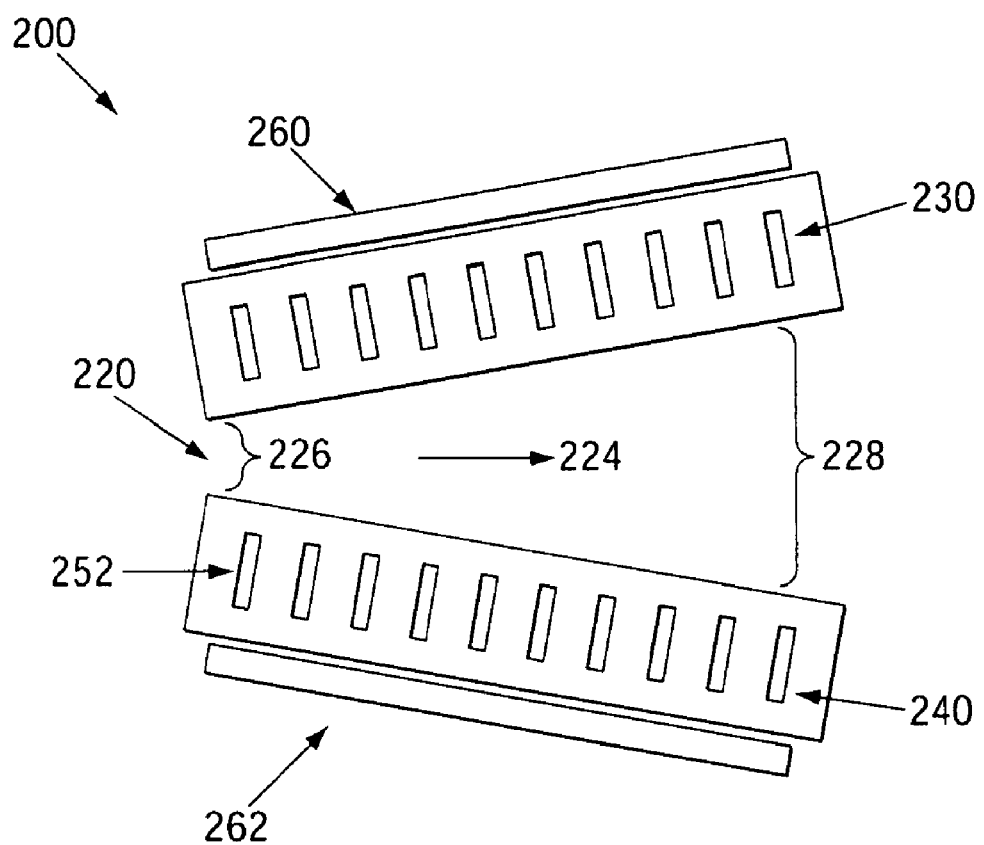
FIG. 3 show a schematic representation of another diverging channel design, according to one embodiment of the invention.

In some embodiments, the electric field applied to the channel in a first region of the channel may be different than that applied to the channel in the second region. In some embodiments, the electrodes may be positioned to be non-parallel with respect to each other. For example, as shown in FIG. 3, device 200 comprises electrodes 260 and 262 positioned in a non-parallel arrangement with respect to one another on opposing sides of channel 220. An electric field may be formed in an orientation perpendicular to the primary direction of fluid flow within the channel, wherein, at various locations within the channel, the electrodes may be separated by different distances and, thus, may have different electric fields. As a result, the electric field in region 226 of channel 220 may be different than that in region 228 of channel 220. Alternatively, a series of electrode pairs may be placed on opposing sides of the diverging channel, wherein the distance between electrode pairs and the voltage applied between various electrode pairs may be the same or different at various locations within the channel.

Use of a diverging channel design may be advantageous in that a pH gradient may be formed and stabilized rapidly within the device and the mixture of species may be separated with high resolution. For example, a mixture may initially be exposed to a portion of the channel having a narrow channel width, wherein the distance between electrodes is small and a pH gradient may be quickly established and maintained. As the channel subsequently diverges, the mixture may be flowed to a portion having a relatively larger channel width, allowing for a greater degree of separation between species (e.g., higher resolution). Thus, a diverging channel configuration may incorporate advantageous features of various FF-IEF device configurations, resulting in a highly resolved fluid sample in a short sample residence time.

In some embodiments, the present invention provides devices for separating a mixture of species, wherein the device comprises a series of regions in which the separation takes place, the regions fluidly connected to one another and arranged in tandem within a continuous channel. Such an arrangement may be referred to as a "tandem" device configuration. Each region of the tandem device may comprise at least two electrodes positioned on opposing and, optionally, external, sides of a portion of the continuous channel to form an electric field substantially perpendicular to the primary direction of fluid flow. For example, the device may comprise a first region comprising a first channel and at least two electrodes positions on opposing sides of the first channel, and a second region comprising at least two channels fluidly connected to the first channel. The second region may also comprise at least two electrodes positioned on opposing, external sides of each of the at least two channels and arranged to form an electric field as described herein. Upon application of an electric field, a pH gradient may be established in each region in a gradient orientation that is perpendicular to the primary direction of fluid flow. Use of a tandem device configuration may be advantageous in that a mixture of species may be separated or purified at multiple locations within the device, allowing for higher resolution of species and, in some cases, with shorter sample residence time. Also, the pH gradient within each region may be selected and maintained independent of another region.

Figure 4:
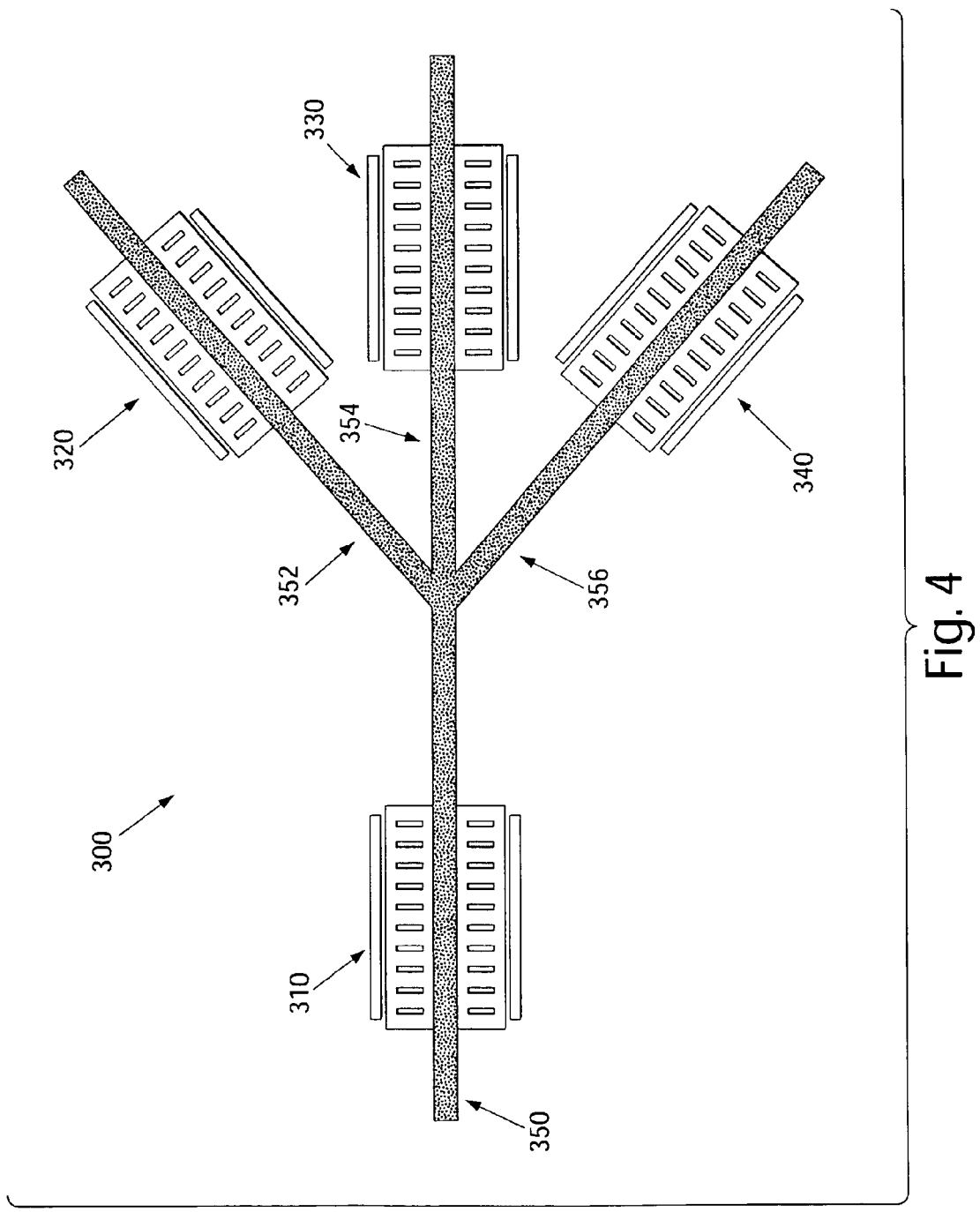
FIG. 4 show a schematic representation of a tandem channel design, according to one embodiment of the invention.

In the illustrative embodiment shown in FIG. 4, device 300 comprises a channel 350 fluidly connected to channels 352, 354, and 356, forming a continuous channel having an inlet and one or more outlets. Channel 350 comprises a region 310 comprising at least two electrodes positioned on opposing sides of channel 350 for separation of a mixture of species, as described herein. Channels 352, 354, and 356 also comprise, respectively, regions 320, 330, and 340, each of which comprise at least two electrodes positioned on opposing sides of the channel, as described herein. Upon application of an electric field, pH gradients may be established in each of regions 310, 320, 330, and 340, wherein the pH gradients of the regions may be the same or different.

In operation, a fluid sample comprising a mixture of species may be introduced into channel 350 and may flow through region 310, wherein a pH gradient may be established to separate the mixture of species in the direction of the gradient (e.g., the gradient orientation). In some cases, the gradient orientation may be perpendicular the primary direction of fluid flow such that the species are separated across the width of the channel in the gradient orientation. Channel 350 is fluidly connected to channels 352, 354, and 356 such that at least a portion of fluid sample flowing from region 310 may flow into regions 320, 330, or 340 via channels 352, 354, or 356, respectively. Portions of the fluid sample may then be exposed to an additional pH gradient for further separation along the gradient orientation. The pH gradient in regions 310, 320, 330, and 340 may be the same or different, and may be suited to a particular application. Portions of the fluid sample may then be flowed to another region of the device for further treatment or to one or more outlets for sample collection.

Individual regions within the tandem device configuration may be selected to suit a particular application. For example, electrodes in individual regions of the tandem device may be arranged as described herein. In some cases, the electrodes may be arranged in a parallel configuration. In some cases, the electrodes may be arranged in a non-parallel configuration. Additionally, the pH gradient established in an individual region may be selected to suit the type of separation desired at a particular location of the device. The pH gradient may be the same or different in various regions, and the individual regions may also be selected to have a particular flow rate or sample residence time. The present invention advantageously provides the ability to independently select and control the channel dimensions, configuration, electric field, pH gradient and, hence, separation ability, of an individual region, independent of other regions of the device.

For example, each region may have a particular length, width, height, diameter, or other dimension or parameter that may affect the pH gradient formed within the region. The regions may be arranged in any order within the device to suit a particular application. In some cases, the fluid sample may first be exposed to a region having a relatively narrow channel, and may be subsequently exposed to a region having relatively wide channel. Alternatively, the fluid sample may first be exposed to a region having a relatively wide channel, and may be subsequently exposed to a region having a relatively narrow channel. In some cases, the device may comprise a series of regions, each region having the same channel length. In some cases, the device may comprise a series of regions having different channel lengths, arranged in a manner to suit a particular application.

Additionally, the device may be arranged to include any number of regions fluidly connected to one another. In the embodiment shown in FIG. 4, a single region is shown to be fluidly connected to three, downstream regions. This embodiment is shown by way of example only and it should be understood that the number and arrangement of regions may be selected to suit a particular application. In some cases, the device may comprise at least 2, at least 4, at least 12, or, in some cases, at least 24 regions. In some cases, the device may have a plurality of regions and a plurality of outlets fluidly connected to the regions for sample collection. For example, the device may be constructed and arranged such that a portion of fluid sample may be collected from a number of outlets, such that each outlet dispenses the fluid sample into a well of a well plate, i.e., a 96-well plate.

The pH gradients within the individual regions of any device of the invention may be the same or different, as described herein. In some cases, the pH gradients of each region may span a different pH range. In some cases, the pH gradient of each region may have a different rate of change in pH unit per mm in the gradient orientation. For example, different pH gradients may span the same pH range but may exhibit a different rate of change in pH unit/mm across the channel in the gradient orientation. In other cases, different pH gradients may span different pH ranges but may exhibit the same rate of change in pH unit/mm across the channel in the gradient orientation. In some case, different pH gradients may span different pH ranges and may exhibit different rates of change in pH unit/mm across the channel in the gradient orientation.

For example, a first region may comprise a pH gradient having a wide pH range while a second region may comprise a pH gradient having a narrow pH range. A fluid sample comprising a mixture of species may pass through the first region and the species may be separated in accordance with the wide pH gradient, and a portion of the fluid sample from the first region may then flow to a second region comprising a pH gradient having a different pH range. In an illustrative embodiment, the pH gradient of the first region may have a pH range from 1.0 to 9.0 in the direction of the gradient orientation such that a mixture of species is separated across the channel in the direction of the pH gradient. That is, fluid sample flowing from the first region may comprise a first set of species positioned within the portion of the channel having a pH range of, for example, 1.0 to 3.0, a second set of species positioned within the portion of the channel having a pH range of 3.0 to 6.0, and a third set of species positioned within the portion of the channel having a pH range of 6.0 to 9.0. The first, second, and third sets of species may be flowed to separate downstream regions comprising, respectively, pH gradients having pH ranges of 1.0 to 3.0, 3.0 to 6.0, and 6.0 to 9.0, in the direction of the gradient orientation. The downstream regions may also have a different rate of change in pH unit/mm across the channel in the gradient orientation such that exposure of any portion of the fluid sample to the downstream region may allow for improved separation (e.g., improved resolution) of the species.

Devices of the invention may have any dimension suited for a particular application. In some cases, the devices include at least one channel having a cross sectional dimension of 0.01 mm, 0.05 mm, 0.1 mm, 0.5 mm, 1.0 mm, 3.0 mm, 5.0 mm, 10 mm, 50 mm, 100 mm, or greater. In some embodiments, the channel cross section may be 1.0 mm or 3.0 mm. For example, the channel may be a narrow slit having the dimensions, 1.0 mm×0.05 mm. Cross section, in this context, is measured perpendicular to the central axis of a channel. In some cases, the channel is sized such that all cross sections at one or more locations in the channel (i.e., all dimensions perpendicular to the central axis) have dimensions as noted above. In some cases, the device may have at least one cross-sectional dimension less than 10 mm, less than 5.0 mm, less than 3.0 mm, less than 1.0 mm, or less than 0.5 mm. The length of the channel, or the length of an individual region in a tandem device, may be, for example, 5.0 mm, 10 mm, 20 mm, 30 mm, 50 mm, 100 mm, or greater.

Another aspect of the invention provides method for separating (e.g., purifying) a mixture of species. For example, the mixture may comprise a mixture of biological molecules, such as proteins, or other species having isoelectric points, i.e., other species having the ability to migrate to a particular location in an electric field. The method may comprise providing a device as described herein, having at least a first region and a second region comprising different pH gradients. The pH gradients may be established within each region upon application of an electric field. The method may comprise exposing a fluid sample comprising a mixture of species to the first region such that the fluid sample is affected by the first pH gradient. At least a portion of the fluid sample from the first region may then be exposed to the second region such that the fluid sample is affected by the pH gradient in the second region, thereby separating the mixture of species.

The method may further comprise recovery of the separated portions of the fluid sample via one or more outlets. In some cases, the present invention may involve the use of greater than 1, greater than 3, or greater than 9 outlets. Some embodiments may comprise the use of an even greater number of outlets (e.g., greater than 50, 100, 150, or more). For example, the number of outlets may correspond to the number of wells in a well plate, i.e., a 96-well plate. In some cases, it may be desirable to maintain a substantially uniform pressure distribution among the plurality of outlets, for example, to maintain the pressure of the overall device and/or to facilitate uniform dispensing of the separated (e.g., purified) fluid sample. Some methods may involve establishing a large pressure drop across the plurality of outlets, to minimize the effect of any minor fluctuations in pressure between various outlets. In other cases, the outlets may comprise tubing or other conduits that may be positioned such that the fluid sample exiting the device must travel in a vertical direction (e.g., vertically upward) before being dispensed from the device. For example, a well-plate may be positioned in a location above the device, and fluid sample may flow through tubing from the device to the well-plate. This configuration may increase hydrostatic pressure in at least some of the outlets, and may aid in minimizing the effects of any minor fluctuations in pressure between various outlets.

Devices of the invention may be operated using a wide range of flow rates. In some cases, the flow rate may be substantially uniform throughout the device. In some cases, the flow rate may be different in various regions of the devices. For example, some methods may involve a longer sample residence time at a particular location within the device to enhance separation of species within a mixture. In some case, the flow rates may be 10 microliters/hour, 50 microliters/hour, 100 microliters/hour, 200 microliters/hour, 300 microliters/hour, 400 microliters/hour, 500 microliters/hour, or greater. It should be understood other flow rates may be used to suit a particular application. In some cases, a relatively high flow rate may be used in a relatively small channel. For example, the device may comprise a channel having a cross-sectional dimension of less than 10 mm (e.g., 1.0 mm, 3.0 mm), wherein the flow rate within the channel is between 100-500 microliters/hour. In some cases, the flow rate in the channel may be between 100-500 microliters/hour and the voltage applied to the channel may be at least 1 V, 10 V, 20 V, 50 V, 100 V, 500 V, 1000 V, 1500 V, or greater. For example, a voltage between 20-100 V may be applied to a channel having a cross-sectional dimension of about 1.0 mm. In some cases, the voltage may be between 100-1500 V, for example, in a diverging channel design. Of course, it should be understood that other combinations of channel cross-sectional dimension, flow rate, and/or voltage may be used to suit a particular application.

As described herein, a pH gradient may be established, upon application of an electric field, within one or more locations of the device and in a direction that is substantially perpendicular to the primary flow of fluid. As used herein, a "pH gradient" refers a range of pH units distributed with respect to a distance, i.e., a distance across a channel. The pH gradient may span a particular range of pH units and may have a rate of change of pH unit per distance (e.g., m). For example, the pH gradient may span a many pH units over a relatively short distance (e.g, a "steep pH gradient"). Alternatively, the pH gradient may span the same or fewer pH units over a relatively longer distance (e.g, a "shallow pH gradient"). The pH gradient may be oriented in a direction that is non-parallel to the primary direction of fluid flow. Mixture of species exposed to such pH gradients, as described herein, may be separated or resolved along the pH gradient on the basis the isoelectric points of the individual species.

The pH gradient may be established by the use of a mixture of amphoteric molecules (e.g., ampholytes) within the channel which, in the presence of an electric field, can migrate to their isoelectric point thereby producing a pH gradient. In some cases, an additional buffer may also be added to stabilize formation of the pH gradient within the device. Those of ordinary skill in the art would be able to select such ampholytes and/or buffers suitable for use in the context of the invention.

In some embodiments, other materials may be utilized alone or in combination with ampholytes/buffers to improve the stability of the pH gradient and/or accelerate formation of the pH gradient. In some cases, one or more materials may be positioned in proximity to the channel in which the pH gradient is formed, wherein the materials are capable of affecting the pH gradient within the channel upon application of an electric field. In some cases, a first material is placed on one side of the channel and a second material is placed in an opposing side of the channel, wherein the first and second materials exhibit different pH values under essentially the same conditions. For example, an acidic material and a basic material may be placed on opposing sides of a channel such that, upon application of an electric field, the acidic material and basic material may facilitate formation of and/or stabilize a pH gradient therebetween. In devices comprising such materials, the pH gradient may be formed and/or stabilized at least 1.0, 2.0, 5.0, 10.0, 50.0, or, in some cases, at least 100 times faster than an essentially identical device lacking the materials, under essentially identical conditions.

In some embodiments, the materials may form sidewalls of the channel, at least partially defining the channel. As shown in FIG. 1, device 10 comprises a channel 20 defined, partially, by material 30 and material 40. Material 30 may comprise a material having a pH less than 7 (e.g., an acidic material) and material 40 may comprise a material having a pH greater than 7 (e.g., a basic material). Device 10 also comprises electrodes 60 and 62, as described herein. Materials 30 and 40 may be in electrical communication with electrode 60 and 62 such that, upon application of an electric field, Materials 30 and 40 are capable of affecting the pH gradient in channel 20. Device 10 may further comprise a series of structural features 50 (e.g., posts) which may provide structural support for the device and/or material. Such materials and features can be incorporated into any device described herein. For example, as shown in FIG. 2, diverging device 100 may comprise materials 130 and 140, which may partially define channel 120 and may affect the pH gradient formed in channel 120. Device 100 may further comprise a series of structural features 152, as described herein. Similarly, as shown in FIG. 3, diverging device 200 may comprise materials 230 and 240, which may partially define channel 220 and may affect the pH gradient formed in channel 220. Device 200 may further comprise a series of structural features 252, as described herein.

Figure 5A:
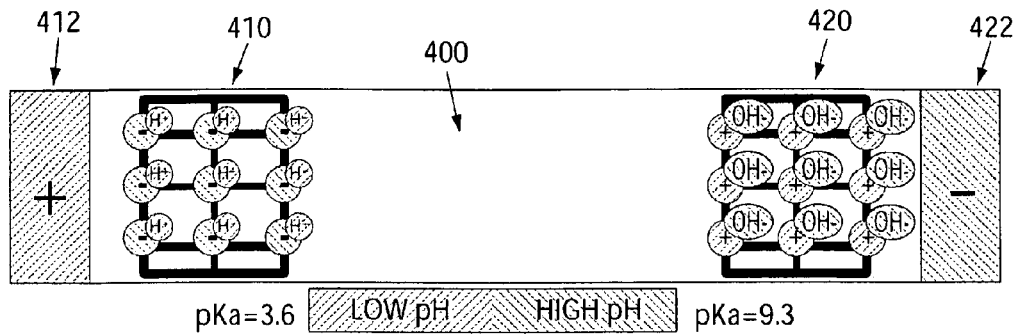
FIG. 5 shows, schematically, the establishment of a pH gradient in a FF-IEF channel comprising an acidic gel and a basic gel on opposing sides of the channel.
Figure 5B:
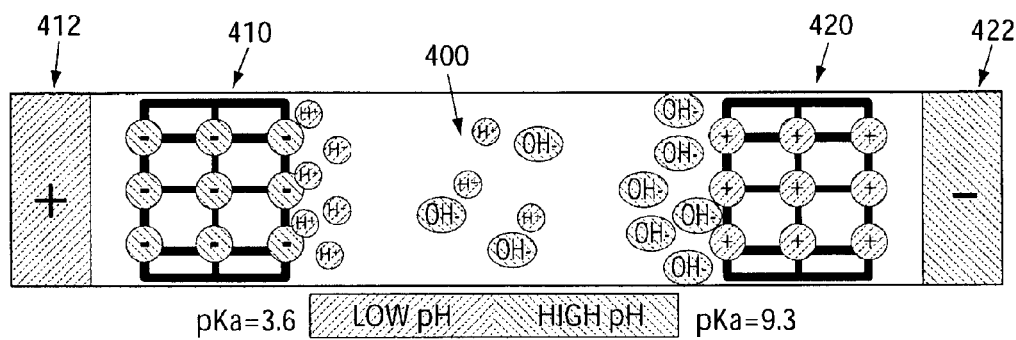
Figure 5C:
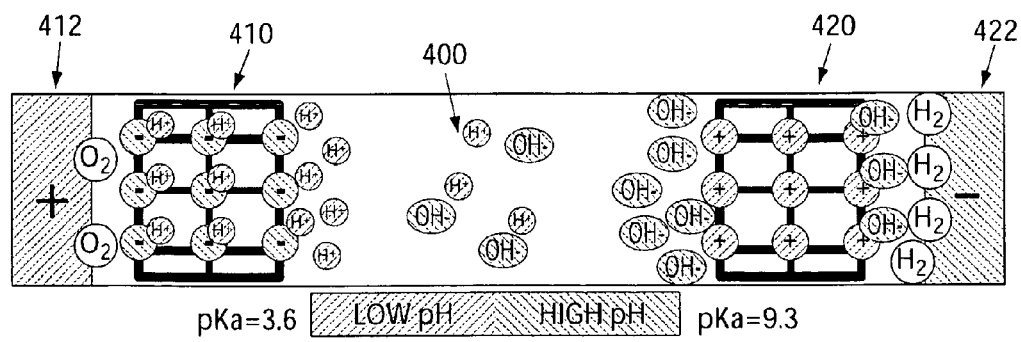

In some embodiments, the material may be a polymeric material comprising either cationic or anionic groups covalently bonded to the polymeric material. For example, a first material may comprise covalently-bound cationic species and a second material may comprise covalently-bound anionic species. In some cases, the polymeric material comprising charged functional groups may be a gel (e.g., a functionalized gel). As shown by the illustrative embodiment in FIG. 5A, channel 400 may comprise a material 410 and a material 420 positioned on opposing sides of channel 400. Material 410 may comprise anionic groups covalently bonded to the polymeric material, while material 420 may comprise cationic groups covalently bonded to the polymeric material. Cathode 412 and anode 422 may be positioned on opposing sides of channel 400. In the absence of an electrical field, the anionic and cationic groups may be associated with their respective counterions (e.g., protons, hydroxide ions) such that the materials are in neutral form. (FIG. 5A) However, upon application of an electric field, the counterions may migrate into the channel such that protons accumulate on one side of the channel, lowering the pH of that portion of the channel and forming an "acidic side" of the channel, while hydroxide ions accumulate on an opposing side of the channel, raising the pH of that portion of the channel and forming a "basic side" of the channel. (FIG. 5B) The establishment of an acidic side and a basic side within the channel may facilitate formation of and/or stabilize a pH gradient therebetween. The acidic and basic sides of the channel may be maintained by a continuous supply of protons and hydroxide ions, respectively, generated by electrochemical reactions that may occur at the electrode surface. (FIG. 5C)

Polymeric materials (e.g., gels) functionalized with (e.g., bonded to) ionic groups may be useful in devices of the invention. The pH gradient of a particular region of the device may be tailored based on the selection of polymeric material (e.g., functionalized gels) employed. For example, the composition of the polymeric material may be altered with respect to the number and types of ionic functional groups contained within the polymeric material, thereby modulating the properties of the pH gradient formed. Those of ordinary skill the art would be able to select and synthesize such materials for use in the invention.

In one set of embodiments, the functionalized gels may be formed by polymerization of a mixture comprising monomeric species and functional group precursors. For example, the mixture may comprise acrylamide monomers and commercially available immobilines (e.g., as the functional group precursor) having a selected pH, such that polymerization of the mixture may produce a polyacrylamide material having the selected pH. In some cases, the monomeric mixture may be positioned within the device and may be polymerized in situ. For example, a fluid, monomeric mixture may be introduced (e.g., injected) into a region constructed to contain the functionalized gel, such as a reservoir positioned adjacent the channel, and the monomeric mixture may be polymerized upon exposure to a source of external energy. That is, the source of external energy may be used to initiate polymerization. The source of external energy may be an electric, magnetic, optical, acoustic, electromagnetic, or mechanical field. In some embodiments, the source of external energy is electromagnetic radiation including ultraviolet (UV) light. In one embodiment, a monomeric mixture may be injected into a region of the device and may be photochemically polymerized by exposure to UV light. In some cases, the source of external energy may be a chemical species. For example, a mixture comprising monomeric species and functional group precursors may be exposed to a chemical species to initiate polymerization and/or functionalization. In some cases, the chemical species (e.g., a peroxide initiator species) may generate a radical for radical polymerization and/or functionalization of monomeric species and/or functional group precursors. Those of ordinary skill in the art would be able to select suitable chemical species for use as initiators in various polymerization reactions.

Devices and methods as described herein may be useful in the separation of species, often with operating times an order of magnitude faster than known techniques. The present invention may also be used in combination with other separation and/or purification techniques, such as SDS-PAGE, immunoblotting, chromatography, centrifugation, crystallization, and the like. The additional separation and/or purification techniques may be performed at a location within the device, or may be performed after the sample or sample fractions have exited the device.

As described herein, the present invention may be useful in the separation of a mixture of species, including essentially any species (e.g., molecule) having an isoelectric point, i.e., having an electrophoretic mobility that may change with respect to pH. In some cases, the mixture of species may comprise particles having an isoelectric point and having an average particle size between 1 nm and 1000 microns, between 2 nm and 500 microns, or, in some cases, between 2 nm and 100 microns. The average particle size may be determined using microscopy (e.g., optical or electron microscopy). In some cases, the species may be a biological molecule such as a protein. In some cases, the species may be a colloid. The fluid sample may comprise additional components, such as ions, salts, or other impurities, with little or no affect on the ability of the device to separate the mixture of species. The fluid sample may comprise solvents including aqueous and non-aqueous (e.g., organic) solvents, or combinations thereof. In some cases, the fluid sample may comprise an aqueous solution containing biological species. In some cases, the fluid sample may be at least 1 microliter, at least 5 microliters, at least 10 microliters, at least 50 microliters, at least 100 microliters, at least 250 microliters, or, in some cases, at least 500 microliters or greater. In other embodiments, the fluid sample may have a volume of 1 microliter or less, or several hundred nanoliters or less. It should be understood that devices as described herein may be constructed to accommodate essentially any volume of fluid sample.

Materials suitable for use as functionalized gels may include, for example, materials comprising acidic or basic groups capable of responding to an electric field. The material may also allow for the diffusion of ions or other electroactive species through the material. In some cases, the material may be a gel. As used herein, the term "gel" is given its ordinary meaning in the art and refers to a structure in which polymer chains may be crosslinked to form a network, wherein the network may be able to trap and contain fluids. The gel may comprise a polymeric material having ionic functional groups covalently bonded to the polymeric material. In some embodiments, the gel may be a hydrogel, including a crosslinkable hydrogel, or a sol-gel. The term "hydrogel" refers to water-soluble polymer chains that are crosslinked in the presence of water to form a network. In some embodiments, the gel may be a sol-gel. A "sol-gel" refers to a colloidal suspension capable of being gelled to form a solid. In some cases, the sol-gel may be formed from a mixture of solid particles (e.g., inorganic salts, silica, and/or alkoxides) suspended in a liquid, wherein a series of reactions including hydrolysis and polymerization reactions may be performed to form a colloidal suspension. The particles may condense in a new phase, the gel, in which a solid macromolecule is immersed in a solvent.

Examples of polymeric materials capable of forming gels include, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups. Other examples of polymeric materials include polyvinylbutryl, polyvinylpyridyl, polyvinyl pyrrolidone, polyvinyl acetate, acrylonitrile butadiene styrene (ABS), ethylene-propylene rubbers (EPDM), EPR, chlorinated polyethylene (CPE), ethelynebisacrylamide (EBA), acrylates (e.g., alkyl acrylates, glycol acrylates, polyglycol acrylates, ethylene ethyl acrylate (EEA)), hydrogenated nitrile butadiene rubber (HNBR), natural rubber, nitrile butadiene rubber (NBR), certain fluoropolymers, silicone rubber, polyisoprene, ethylene vinyl acetate (EVA), chlorosulfonyl rubber, flourinated poly(arylene ether) (FPAE), polyether ketones, polysulfones, polyether imides, diepoxides, diisocyanates, diisothiocyanates, formaldehyde resins, amino resins, polyurethanes, unsaturated polyethers, polyglycol vinyl ethers, polyglycol divinyl ethers, copolymers thereof, and those described in U.S. Pat. No. 6,183,901. Those of ordinary skill in the art can choose appropriate polymers that can form a gel, as well as suitable methods of crosslinking, based upon general knowledge of the art in combination with the description herein. In some cases, the polymeric material comprises polyacrylamide.

The electrodes may be any material capable of conducting charge. In some cases, the electrode comprises a metal, metal oxide, metal nitride, carbon, or a polymer. Examples of materials suitable for use as electrodes include, but are not limited to, metals or metal-containing species such as gold, silver, platinum, or indium tin oxide (ITO). In some cases, the electrodes may comprise platinum. Those of ordinary skill in the art would be able to select electrode materials suitable for use in the invention.

Devices described herein can be fabricated of a polymer, for example an elastomeric material such as poly(dimethylsiloxane) (PDMS) using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the network, a flat substrate, for example, a glass slide, silicon wafer, or polystyrene surface may be placed against the PDMS surface and may be held in place by van der Waals forces, or may be fixed to the PDMS using an adhesive. To allow for the introduction and receiving of fluids to and from the network, holes (e.g., 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue. Examples of methods of manufacturing devices such as these are provided in U.S. Pat. No. 6,645,432, incorporated by reference in its entirety herein.

EXAMPLES

Example 1

The following example describes the theoretical Basis for IEF, according to an illustrative embodiment of the invention. Mass transport equations were used as the starting point to formulate expressions to describe isoelectric focusing. The conservation equation for species in solution experiencing an electrophoretic force is given by Equation (1), below:

$$\frac{\partial C_i}{\partial t} = \underline{\nabla} \cdot (D_i \underline{\nabla} \cdot C_i - E z_i \omega_i C_i) \quad (1)$$

In Equation (1) the concentration of a species C, is a function of position and time, electric field E, variable charge $z_i$, constant mobility $\mu_i$ and its diffusion constant $D_i$. In order to understand the effect of geometry and physical parameters on focusing, it may be helpful to non-dimensionalize the conservation equation for one-dimensional transient focusing and make two assumptions: i) a linear pH gradient is established over the total width, w, and ii) the species has a linear charge behavior in the channel ($dz_i/dx=\Delta z_i/L$=constant). Non-dimensionalizing and expanding the derivative results in Equation (2):

$$\frac{\partial \Theta}{\partial \tau} = \frac{1}{Pe_e} \frac{\partial^2 \Theta}{\partial \eta^2} - \Theta - \frac{\partial \Theta}{\partial \eta}(\eta - \eta_{pI}) \quad (2)$$

The dimensionless quantities in Equation (2) are defined as $\Theta=C_i/C_{i,0}$, $\eta=x/L$, $\tau=Et\omega\Delta z/L$, and $Pe_e=E\omega L\Delta z/D$. The location where the species focuses is defined by $\eta_{pI}$. The ratio of electrophoretic to diffusive fluxes, $Pe_e$, is similar to a Peclet number. This number must be >1 for electrophoresis to dominate the system. At steady state, Equation 2 reduces to Equation 3, with the solution given by Equation 4, in dimensionless form:

$$0 = \frac{1}{Pe_e} \frac{d^2\Theta}{d\eta^2} - \Theta - \frac{d\Theta}{d\eta}(\eta - \eta_{pI}) \quad (3)$$

$$\Theta = \sqrt{\frac{Pe_e}{2\pi}} \exp\left(-\frac{(\eta-\eta_{pI})^2}{2} Pe_e\right) \quad (4)$$

The Gaussian distribution of Equation 4 has a standard deviation of $Pe_e^{-1/2}$. By defining separation distance as three standard deviations (87% of the peak area), this leads to Equation 5, equivalent to the known results for the minimum resolvable difference in pI. Here, resolution, Res, is defined as the minimum difference pI divided by the pH range within the channel:

$$\frac{\Delta pI_{min}}{\Delta pH} = 3\sqrt{\frac{D}{E\omega L \Delta z}} = \frac{1}{Res} \quad (5)$$

At excessively high electric fields, detrimental phenomena such as Joule heating, electroosmotic flow, and precipitation can reduce the opportunity for ideal focusing. Therefore, for any sample composition, there may be an optimal electric field strength that maximizes resolution while minimizing negative effects. To examine focusing behavior in a variety of geometries, the electric field (as opposed to applied voltage) was assumed to be the same for every case. For the time scaling in Equation 2, the time scale of focusing (t/τ) increases linearly with respect to channel width, w. From Equation 5, the resolution at steady state increases with $w^{1/2}$. These dependencies may illustrate that, in some cases, there can be a trade-off between short focusing times and resolution when the applied field is constant. This trade-off can be exploited with multiple stages to deliver high resolution separations with a minimal focusing time, analogous to shifting gears in order to maximize a vehicle's acceleration.

Considering instead the case of constant applied voltage (V=EL), the time scale of focusing increases with $w^2$, whereas the steady state resolution is independent of distance. In some cases, however, using a constant voltage for a range of channel widths may be less feasible than maintaining a constant electric field. Applying the high voltages typical in cm-scale IEF (200-500V) to a channel 1 mm in width may result in field strengths of 2-5 kV/cm. Electroosmotic flow can increase by a factor of 10, and joule heating can increase by a factor of 100: a thermally insulated 1 µL, sample with conductivity similar to 2% Ampholine in deionized water (0.3 mS/cm) can be heated at a rate of 300-1800° C./s.

Because the analytical expressions for IEF may assume an established pH gradient and may not consider nonlinear changes in sample conductivity, a 1-D transient IEF model using Jacobian (Numerica Technologies, Cambridge, Mass.) was employed to explore the effect of distance on focusing dynamics. This model assumes electroneutrality and instant pH equilibrium for a mixture of 140 biprotic ampholytes. The model was expanded to accommodate dynamic changes in channel width and applied voltage, to compare focusing dynamics for channels of various widths. A model with 240 spatial points (resulting in 137,613 coupled equations) was used to quickly simulate focusing at these widths, requiring only about 3 hours of CPU time on a 3.8 GHz personal computer. Custom MATLAB programs were used to provide Jacobian self-consistent initialization conditions, as well as to parse and post-process the simulation results.

Figure 6:
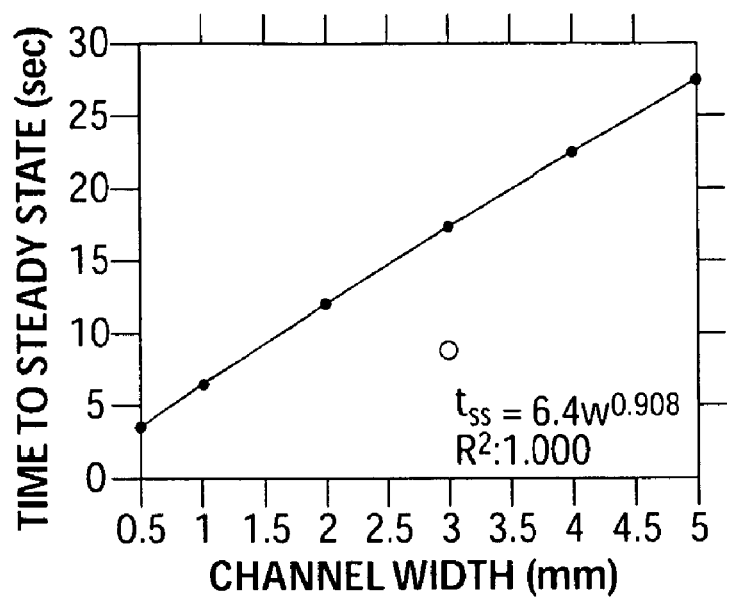
FIG. 6 shows a plot of the time required for a pH gradient to reach steady state ($t_{ss}$), as a function of channel width.
Figure 7:
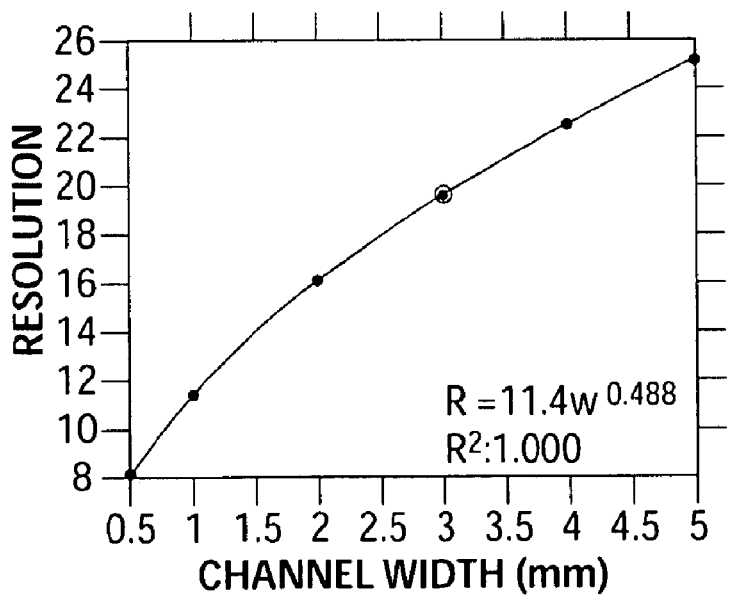
FIG. 7 shows a plot of the resolution (Res) of a pH gradient as a function of channel width, from a Gaussian fit of one of the ampholytes versus channel length for the simulations.

To test the analytical predictions, several simulations were run at various widths and constant average electric field (100V/cm). FIGS. 6-7 show the results of these simulations, illustrating the dynamics of the IEF simulation with respect to channel size. FIG. 6 shows a plot of the time it took to reach steady state ($t_{ss}$) as a function of channel width, while FIG. 7 shows a plot of the resolution (Res), as a function of channel width, from a Gaussian fit of one of the ampholytes versus channel width for the simulations. Also plotted are power equations with two fitted parameters that were expected to describe the simulation results. A nearly linear relationship (exponent of 0.908) existed between focusing time and channel width, as predicted by scaling arguments. The relationship between resolution and channel width also followed the predicted power law behavior, with a fitted exponent of 0.488 versus 0.5 for the analytical case. From the solid lines in FIGS. 6-7, a wider FF-IEF channel had the effect of increasing both focusing resolution and focusing time. A simulation where the channel was instantly widened from 1 to 3 mm after 5 seconds, shown as open circles in FIGS. 6-7, showed that the higher resolution of the 3 mm channel can be reached in half the time (8.70 versus 17.49 seconds to steady state) when the average electric field was held constant at 100 V/cm. The results indicated that the effects of pH gradient formation and changes in conductivity may not significantly alter the idealized focusing behavior of simple ampholytes, underscoring the usefulness of the analytical expressions for IEF.

Example 2

Figure 8:
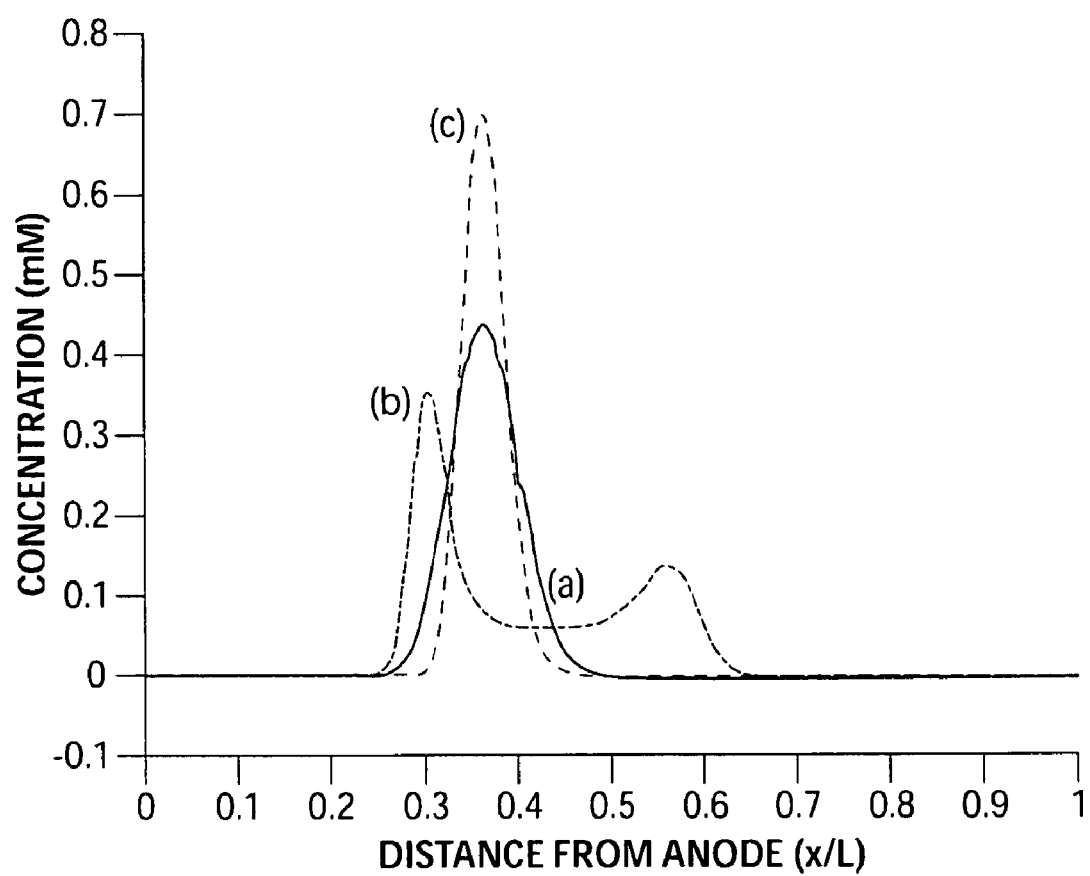
FIG. 8 shows the simulated focusing of BSA under three different geometry configurations at identical field strengths: (a) 1 mm, (b) 3 mm, and (c) 1 mm followed by focusing at 3 mm.

The model described in Example 1 was used to simulate the focusing of a protein, BSA, in a channel either 1 or 3 mm long. FIG. 8 shows the simulated focusing of BSA under three different geometry configurations at identical field strengths: (a) 1 mm, (b) 3 mm, and (c) 1 mm followed by focusing at 3 mm. To better quantify focusing, the simulation used low electric fields (5 V/cm for each case) for slow, low resolution focusing. The resolution (from a Gaussian fit, $R^2>0.999$) of the focusing was 1.6 times greater for the longer channel. Transitioning from a shorter to a longer channel reached this higher-resolution steady state in 40% less time than the 3 mm case. These results show that the simulation results for small amphoteric molecules may also be applicable to large proteins with complicated electrophoretic behavior.

Example 3

Figure 9A:
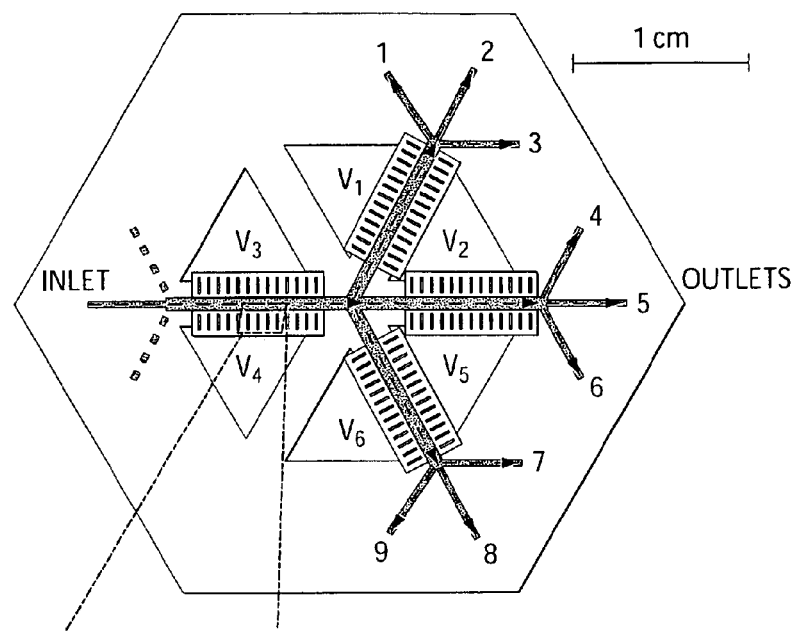
FIG. 9 shows, schematically, (a) a tandem channel design comprising four focusing regions, (b) a channel bordered by posts to define placement of the porous material, and (c) a photograph of a tandem channel design having 9 outlets.
Figure 9B:
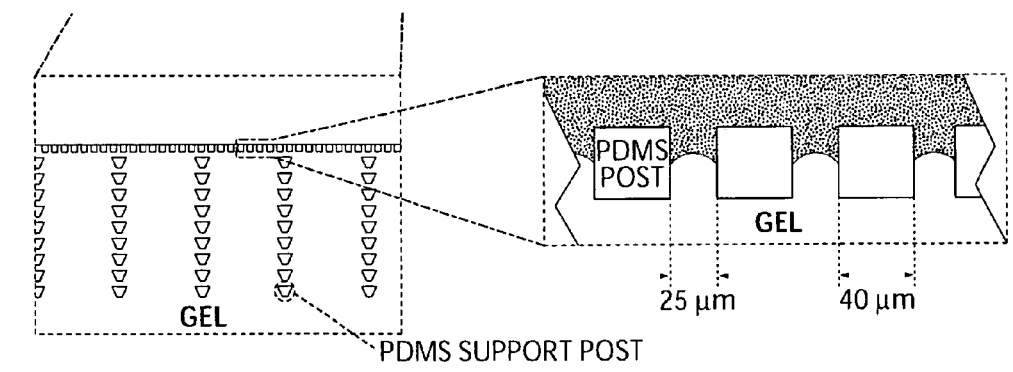

Free flow IEF devices were designed to have a sample channel defined by a porous material capable of allowing ion conduction between the sample channel and the electrode buffer, while preventing fluid convection between the two regions. In this study, a single stage straight channel design 20 mm long by 1 mm wide was compared with a similar straight channel design that was a 30 mm long by 3 mm wide straight channel and a tandem design, as shown in FIG. 9A. The tandem design consisted of four focusing regions: the first IEF stage is a single channel (1 mm wide by 7.62 mm long) that branches into three secondary IEF stages with dimensions identical to the first stage. A split configuration may provide i) a more uniform fluidic resistance for an improved flow field and sample collection, as well as a higher degree of control over the electric field within the device. The designs were based on a PDMS channel bordered by posts to define placement of the porous material without the need for a photo-polymerization mask, as shown in FIG. 9B. Small liquid reservoirs (2 for each straight design, 6 for the tandem design) were manually cut out of the PDMS to contain catholyte and anolyte as well as platinum electrodes, which were connected to an external power source.

The devices were fabricated using standard soft lithography techniques, using the following procedure. A silicon wafer was coated with a layer of SU-8 2050 (MicroChem, Newton, Mass.), which was pattered using a 5080 dpi transparency mask (Pageworks, Cambridge, Mass.). Next, Sylgard 184, (Dow Chemicals, Midland, Mich.) was cast over the SU-8 mold and cured at 70° C. for two hours. After curing, the PDMS was peeled off of the master; individual devices were cut out, and fluidic connections were punched using a 20 gauge luer stub adapter (Becton-Dickinson, Sparks, Md.). When a 23 gauge Luer stub adapter was inserted in to these holes, the connection was self-sealing; no epoxy or glue was necessary. Next, the devices (two at a time) were treated with oxygen plasma for 40 seconds prior to permanently bonding to a 50×75 mm microscope slide. After bonding, the microscope slide was scored and cut with a diamond scribe to separate pairs of devices. Next, the channels were filled with 1% 3-(trimethoxysilyl)propyl methacrylate in ethanol and allowed to dry overnight.

To cast an acrylamide gel within the devices, the following general procedure was followed. The device were rinsed with ethanol, and degassed in a vacuum oven at 70° C. and 50 mmHg for more than 2 hours. Subsequently, the devices were kept under nitrogen using an acrylic glove box (Air Control, Inc., Henderson, N.C.). The monomer solution used in the polyacrylamide devices tested contained 15% total acrylamide (15% T), with 3% of the acrylamide present as bis-acrylamide (3% C) (purchased from PlusOne ReadySol IEF, GE Healthcare, Piscataway, N.J.). Immobilines having a pKa of 3.6 (purchased from GE Healthcare) were added to the monomer solution for the anode side of the device, while immobilines having a pKa of 9.3 (purchased from GE Healthcare) were added to the monomer solution for the cathode side of the device, to a final concentration of 12 mM. To fill the anode side of the device, 60 μL of 1% v/v Triton X-100 (EMD Chemicals, Gibbstown, N.J.), and 6 μL of 10% w/v DMPA (2,2-Dimethoxy-2-phenylacetophenone, Sigma-Aldrich, St. Louis, Mo.) in acetone was added to 1 mL of the anode (pKa 3.6) monomer mixture. For the cathode side, 30 μL of 1% Triton and 6 μl, of 10% DMPA was added to 1 mL of the cathode (pKa 9.3) monomer mixture. These anode and cathode monomer mixtures with DMPA and Triton were mixed together at a 2:1 or 1:2 ratio to form the intermediate pH gels used in the tandem design.

These monomer mixtures were cast inside the devices by introducing them to the electrolyte reservoirs, where they were drawn into the device by capillary action. Reaching the hydrophobic PDMS posts at the sample channel, the solution was held in place by surface tension, long enough to polymerize using a UV lamp (354 nm, Spectroline ENF-280C, Spectronics Corporation, Westbury, N.Y.). DMPA was observed to graft the polyacrylamide gel to the PDMS. However, because DMPA is highly soluble in PDMS, incomplete polymerization occurred for very shallow channels, and for long wait times (>5 min) before exposure. To correct for this, long exposure times (2 minutes at a distance of 3 cm) were used to ensure adequate polymerization. After polymerization, the devices were stored under 1% w/v solution of poly (vinyl alcohol) (PVA, MW 146-186 kDa, 87-89% hydrolyzed, Sigma-Aldrich).

Next, platinum wires or foil (0.5 mm diameter or 0.1 mm thickness, Alfa Asear, Ward Hill, Mass.) were used to connect the electrode reservoirs to a high voltage electrophoresis power supply (VWR, West Chester, Pa.). Silicone sealant (ASI 502, American Sealants Inc, Fort Wayne, Ind.) was used to fix the wires in place and to form reservoirs for the anolyte and catholyte buffers. The anolyte used was 100 mM phosphoric acid with 1% w/v hydroxypropyl methyl cellulose (HPMC, Fluka, Buchs, Switzerland) and 1% Triton; the catholyte was 200 mM lysine and 200 mM arginine (10×IEF Cathode Buffer, Bio-Rad, Hercules, Calif.) in 1% HPMC and 1% Triton. To buffer the second stages to an intermediate pH, 50 mM MES (adjusted to pH 5.35) and 50 mM HEPES (adjusted to pH 7.25) buffers, each with 1% HPMC and 1% Triton, were used. Samples were pulled through the device using a multichannel syringe pump (EW-74901-10, Cole-Parmer, Vernon Hills, Ill.) equipped with nine 100 µL gas-tight syringes (Hamilton, Reno, Nev.) set to withdrawal mode. At the inlet of device, a 200 4, pipette tip was simply inserted into the PDMS. This sample reservoir was easily refilled by adding samples into the top of the pipette tip.

The tandem devices were not cooled with known thermoelectric elements, due to the size and layout of the tandem devices. Two cooling strategies were employed for different analyses. For fluorescent samples, the devices were cooled by venting nitrogen gas withdrawn from a liquid nitrogen cylinder over the glass underside of the device mounted on the microscope stage. The forced convection was sufficient to observe focusing. For SDS-PAGE or immunoblot analysis, where in situ observations were not performed, the devices were cooled by placing the device atop an aluminum heat sink (659-65AB, Wakefield Engineering, Pelham, N.H.) inverted (fins down) in a shallow dish. The dish was filled with a sufficient amount of ice water to immerse the fins of the heat sink, effectively keeping the device at or near 0° C.

To apply voltages to the tandem devices, three power supplies were connected in parallel to apply 90V to one reservoir, ($V_1$ in FIG. 9A), 60V ($V_2$ and $V_3$ in FIG. 9A), or 30V to others ($V_4$ and $V_5$ in FIG. 9A), while grounding the remaining reservoir ($V_6$). This configuration resulted in 30V across each focusing region within the device, and minimized electrical interaction between regions.

Example 4

The devices described in Example 3 were employed in the separation of dyes and proteins via FF-IEF. Dye-focusing experiments were conducted with fluorescent low molecular weight pI markers (isoelectric points: 5.1, 7.2, 7.6, and 9.5, Fluka, Buchs, Switzerland). Markers were used at a final concentration of 1 mg/mL. Ampholine 3-10 and NP-40 (Nonident P-40 substitute, Fluka) were added to deionized water (Millipore, Billerica, Mass.) to a final concentration of 2% and 0.5%, respectively.

To visualize the focusing of a fluorescently labeled protein, an Alexa 488 conjugated protein G (purchased from Invitrogen, Carlsbad) was mixed in phosphate buffered saline (PBS, Invitrogen) with 2% Ampholine 3-10 (Fluka) to a final concentration of 80 µg/mL (4 mM). For experiments where the sample was subsequently processed by SDS-PAGE, the sample consisted of unlabeled protein standards for IEF: amylglucosidase, carbonic anhydrase II, trypsin inhibitor, and trypsinogen (IEFM1A-1KT, Sigma-Aldrich) as well as Alexa labeled protein G and Texas Red labeled streptavidin (Invitrogen) were mixed together in PBS with 2% Ampholine to a final concentration of 0.95 mg/mL for the unlabeled protein standards, and 0.24 mg/mL for protein G and streptavidin. Approximately 0.4 mL of sample was used for each experiment.

Quantitative immunoblot assays of total Erk2, phosphorylated Erk (pErk), and Cytochrome c were performed using cell lysates. For narrow pH range focusing, the cells were washed with PBS prior to lysis to remove albumin in the cell media. The lysis buffer consisted of: 1% Triton X-100, 150 mM NaCl, 10 mM β-glycerophosphate, 10 mM $Na_4P_2O_7$, 10 mM NaF, 1 mM $Na_3VO_4$, 10 µg/mL leupeptin, 10 µg/mL pepstatin, and 10 µg/mL chymostatin. To ensure both phosphorylated and unphosphorylated forms of Erk, half of the cell lysate originated from cells was stimulated with 50 ng/mL TNF-α for 10 minutes. The insoluble (pellet) and soluble (supernatant) fractions were isolated by centrifugation (10 min at 20000 g). No other purification steps were performed. Before FF-IEF, the sample was mixed with an equal volume of 8M urea and ampholytes (for the 3-10 pH or 5-7 pH range) were added to a final concentration of 2%. Some samples were prepared with 0.45% NP-40.

Focusing behavior was observed with an inverted fluorescent microscope (Axiovert 200, Carl Zeiss, Inc, Thornwood, N.Y.) with a high speed 8-bit color camera (MF-046C, Allied vision technology GMBH). A FITC filter was used to detect green fluorescence. Full frames were captured with a shutter time between 100 ms and 2.5 seconds, depending on the fluorescent intensity of the sample. The images captured by the camera were subsequently processed by programs written in MATLAB (The Mathworks, Natick, Mass.). Full-color images were desaturated prior to analysis. To find pixel intensity across the width of the channel, 50 to 500 pixels from a steady state image were averaged, and normalized to the maximum intensity.

Following FF-IEF, the collected fractions were mixed with SDS-PAGE tricine sample buffer containing β-mercaptoethanol as a reducing agent and separated on a precast 10 or 12 lane tricine gel according to the manufacturer's instructions. Following electrophoresis, the gel was stained using either a silver staining kit (Thermo Fisher, Portsmouth, N.H.) or Coomassie (Simply Blue, Invitrogen). The setup and run time (approximately an hour) for the IEF separation was equivalent or less than the SDS-PAGE setup and run time.

Immunoblots of total Erk2 (SC1647, Santa Cruz Biotechnology, Santa Cruz, Calif.) and pErk (9101 L, Cell Signaling Technology, Danvers, Mass.) were performed using the same primary antibodies as for flow cytometry at a 1:500 and 1:1000 dilution, respectively. Proteins were separated by SDS-PAGE and transferred to nitrocellulose. After blocking (30-60 min at room temperature), blots were probed overnight at 4° C. in primary antibody, washed 3 times for 5 mM in TBS-T (20 mM Tris-HCl pH 7.5, 150 mM NaCl, 0.1% Tween-20), incubated 1 h at room temperature in secondary antibody (1:5000 IRDye800-conjugated donkey anti-rabbit IgG, Rockland Immunochemicals), and finally washed 3×5 min in TBS-T. Blots were scanned on an Odyssey imaging system (Li-Cor Biosciences).

Figure 10A:
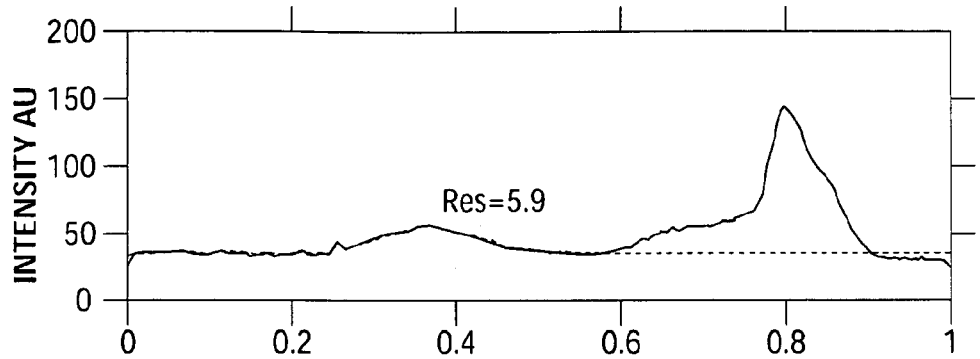
FIG. 10 shows the fluorescence profile of the sample versus distance from the anode (mm) for a sample exiting (a) a first region and (b) a second region of a tandem device.
Figure 10B:
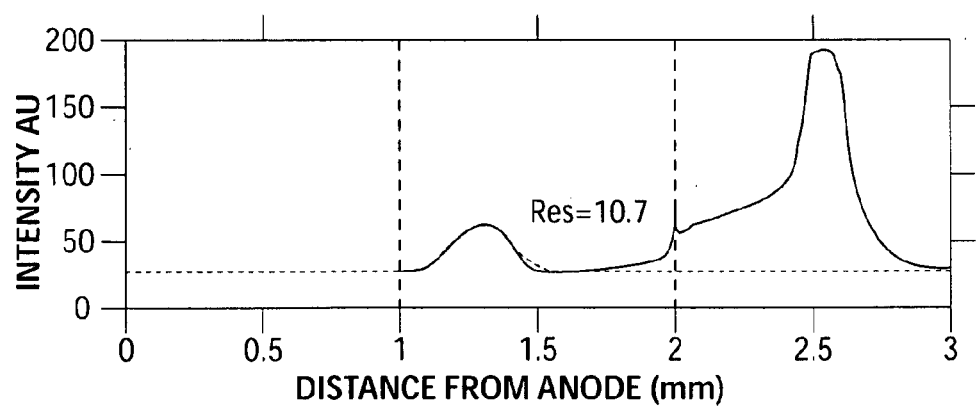
Figure 11:
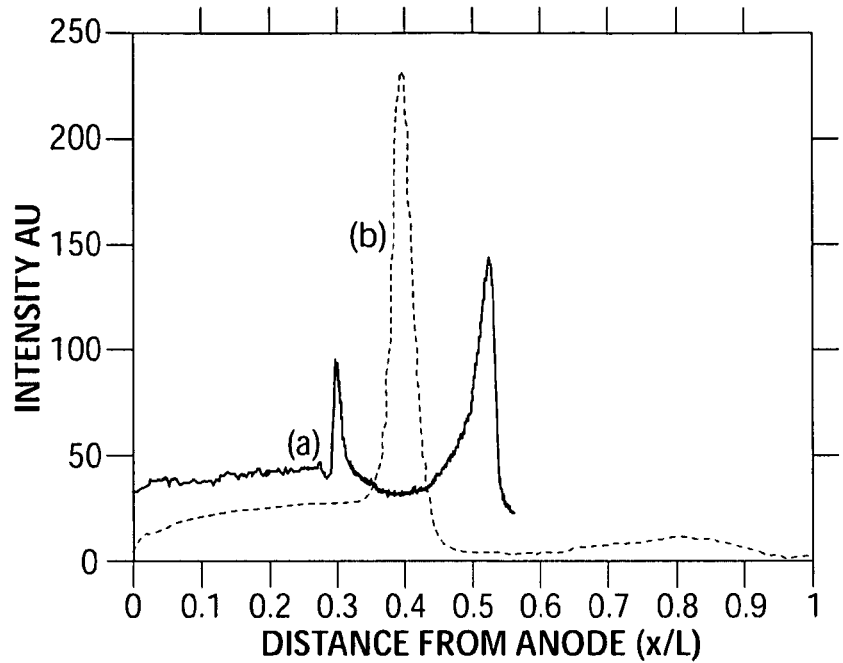
FIG. 11 shows a plot of fluorescence intensity of the Alexa protein G as a function of distance from the anode, as a protein was focused in (a) a straight, 3 mm channel and (b) a straight, 1 mm channel.
Figure 12:
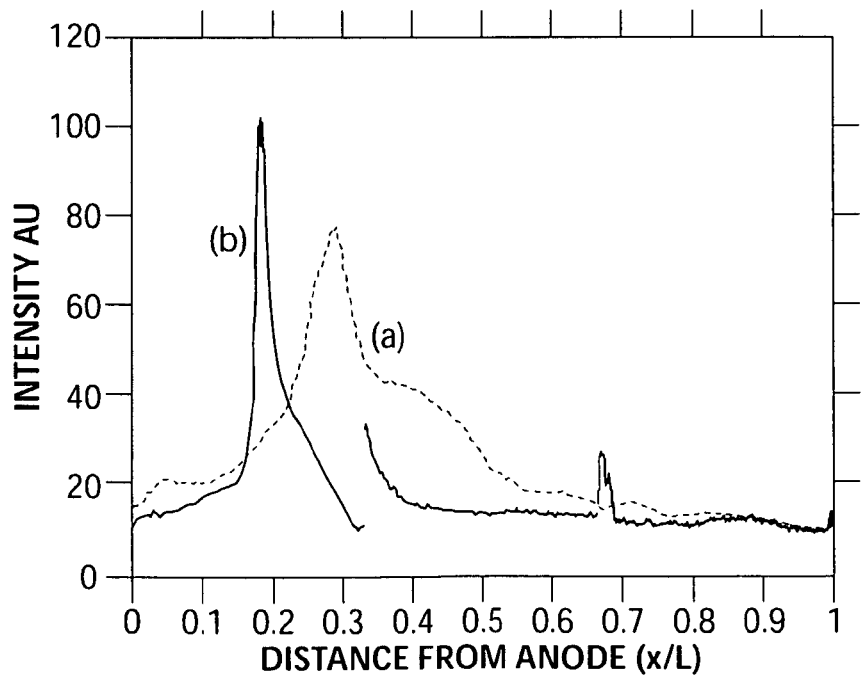
FIG. 12 shows a plot of fluorescence intensity of the Alexa protein G as a function of distance from the anode, as a protein was focused in (a) the first stage of a tandem channel design and (b) the second stage of the tandem channel design.

Fluorescent IEF markers were then focused in the device to observe the effectiveness of tandem stages in increasing resolution. To focus the markers, 75 to 85V were applied across each section of the device for inlet flow rates of 55 mL/s. FIG. 10A shows the fluorescence profile of the sample versus distance from the anode (mm) after the sample exited the first region or stage of the device. Gaussian fits (dotted lines) to the pI 5.1 marker were used to calculate focusing resolution (Res)) according to Equation (5). The steady-state, focusing resolution was calculated to be 5.9 after 6.8 second of focusing. FIG. 10B shows the fluorescence profile of the sample versus distance from the anode (mm) after the sample exited the second region or stage of the device, exhibiting greater resolution and concentration of the markers after an additional 20.4 seconds of focusing. The focusing resolution after the second stage was calculated to be 10.7, consistent with theoretical calculations. The improvement in resolution from the first to second stage (10.7 vs. 5.9) was a factor of 1.81, consistent with the expected value of 1.71 for a 3-fold increase in channel width. FIGS. 11-12 show the focusing of protein G in various design configurations, using the same field strength. FIG. 11 shows a plot of fluorescence intensity of the Alexa protein G as a function of distance from the anode, as the protein was focused in straight channels of varying widths. FIG. 11A shows the fluorescence of the protein when focused in a straight, 3 mm channel (w=3 mm). Only part of the channel could be imaged. FIG. 11B shows the fluorescence of the protein when focused in a straight, 1 mm channel (w=1 mm). After 13 s, focusing of the protein was still incomplete in the straight, 3 mm channel. By contrast, a steady state was reached in less than 9 s in a straight, 1 mm channel.

FIG. 12 shows a plot of fluorescence intensity of the Alexa protein G as a function of distance from the anode, as the protein was focused in tandem channel design. As shown in FIG. 12A, incomplete focusing was observed after 3.4 seconds in the first stage (w=1 mm). However, the protein was tightly focused after an additional 10.2 seconds in the second stage (w=3 mm), as shown in FIG. 12B. The straight, 1 mm channel device reached steady state before the other designs, but with the lowest resolution. The straight, 3 mm channel device required the longest residence time to reach steady state, approximately 22 seconds, as predicted by theory. The tandem device required approximately 14 s of focusing time, but had a final resolution comparable to the wider, straight channel design. However, incomplete fractionation of proteins in the semi-focused first stage resulted in protein G buildup entering stages with pH ranges above its pI. This incomplete focusing resulted in buildup and adhesion on the anode gel in the neighboring stages shown by the solid line in FIG. 12B at x/w=0.33 and 0.67.

Example 5

Figure 9C:
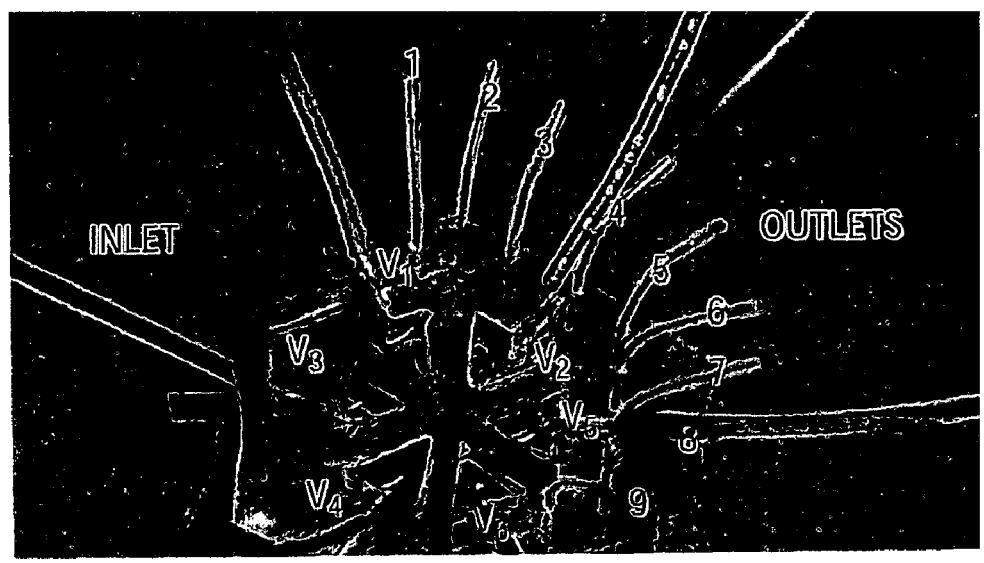
Figure 13:
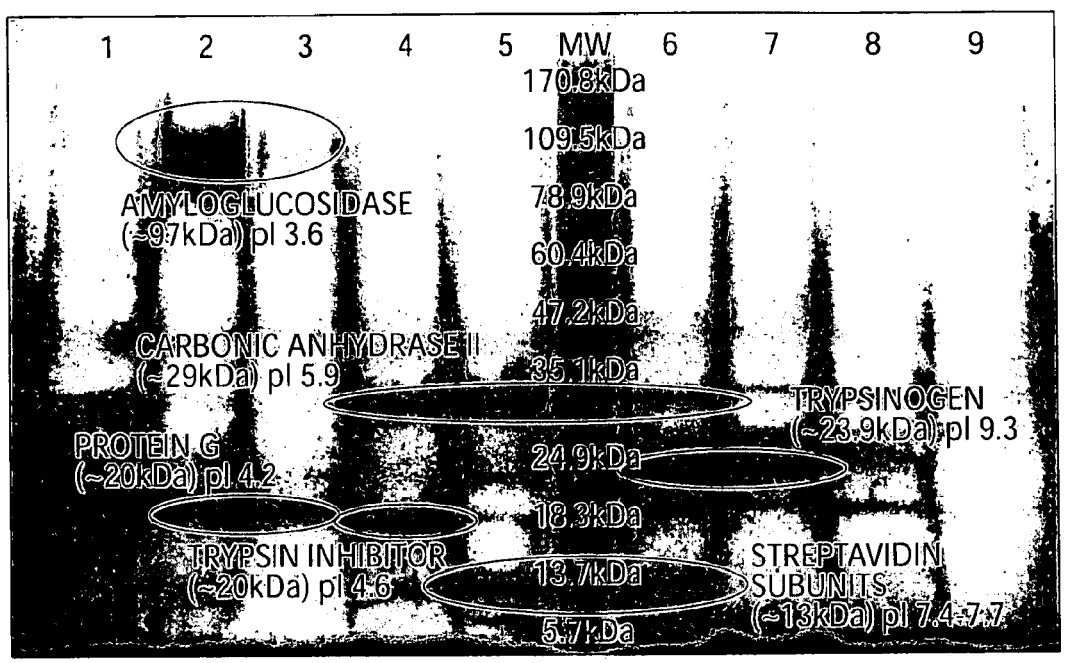
FIG. 13 shows a photograph of the Coomassie stained gel of five model proteins in PBS separated in a 3-10 pH gradient, where each IEF fraction 1-9 was separated in one lane of the gel.

To demonstrate that the tandem FF-IEF device can be used with other orthogonal separations, a mixture of proteins with known pI and molecular weight were separated in the device, and loaded on a SDS-PAGE gel. As shown in FIG. 9C, outlets on the FF-IEF device were numbered from 1 to 9 with outlet #1 corresponding to the lowest pH and outlet #9 to highest pH. FIG. 13 shows a photograph of the Coomassie stained gel of five model proteins in PBS separated in a 3-10 pH gradient, where each IEF fraction 1-9 was separated in one lane of the gel. The sample was processed at 111 nL/s (18 s residence time) and ~150V/cm. The gel showed that the proteins were focused into one, two, or three IEF fractions, and that no two fractions had the same protein composition. The labeled recombinant streptavidin was reduced by the tris-tricene sample buffer into its four subunits appearing at 13.2 instead of 57 kDa. The collected fractions were the integral of an hour of continuous focusing in the device, and the consistent focusing showed that there was minimal drift in device performance. Notably, the pH gradient was compressed in the device due to the high salt concentration, causing fractions 1, 8, and 9 to be empty. Also, carrier ampholytes, which can interfere with detection tools such as mass spectrometry, were easily separated from the proteins in the outlet fractions, staining as a low molecular weight (<1 kDa) band just above the salt front. This 2-D separation required less labor and one-tenth the operating time of a 2-D gel.

For low abundance proteins (e.g., signaling kinases) present in complex samples, detection was performed using affinity techniques such as immunoblotting. The sensitivity of such detection may be strongly dependent on mitigating non-specific binding artifacts.

Figure 14A:
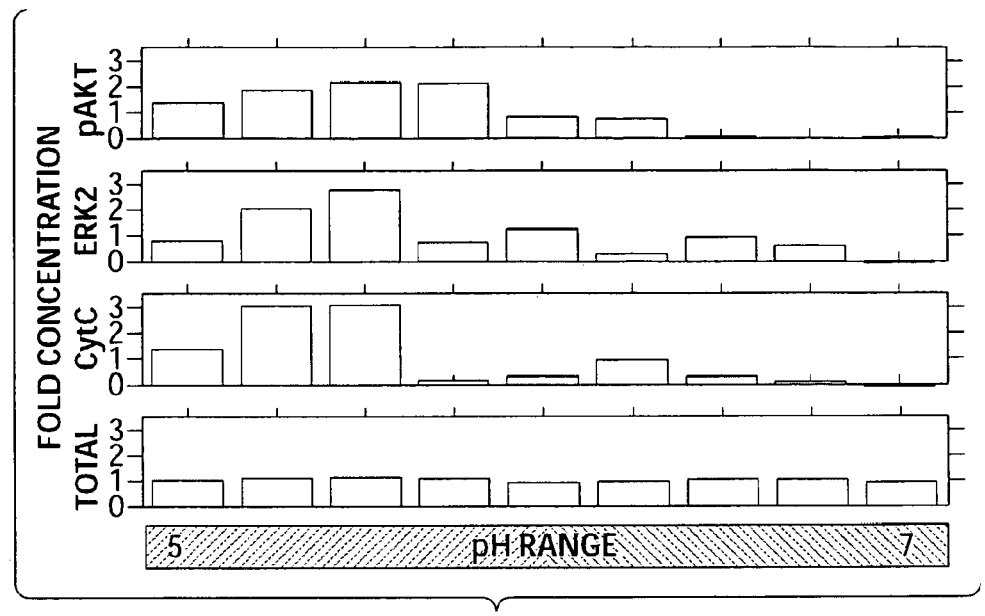
FIG. 14 shows immunoblot and silver stain results for signaling proteins in HeLa cell lysate focused in (a) a 5-7 pH gradient and (b) a 3-10 pH gradient with 0.45% NP-40.
Figure 14B:
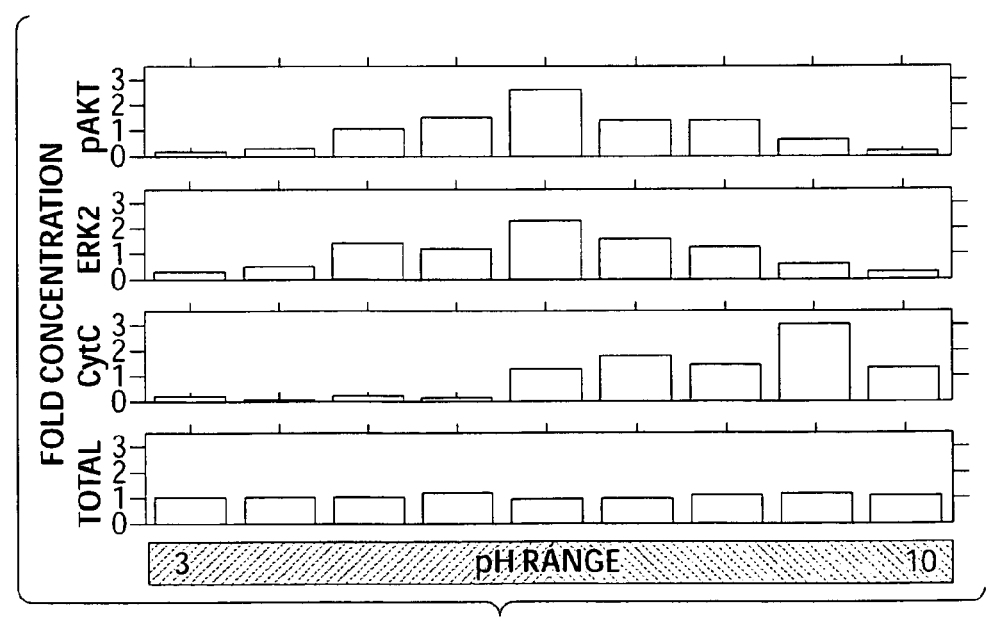

Narrow pH ranges were also used in the device, to separate proteins with similar pI. FIG. 14A shows immunoblot and silver stain results for signaling proteins in whole HeLa cell lysate focused in a 5-7 pH range, in the presence of 4M urea. Bands were scaled to represent fold concentration over the averaged outlet signal. The protein bands corresponding to cytochrome c and pAkt showed reasonable focusing and at least 2-fold enrichment over the lysate alone (control). However, Erk2 and pErk showed weaker focusing, perhaps due to the short focusing time and multiple pIs across the 5-7 range for the various phosphorylated forms of Erk. Notably, cytochrome c was focused to an average pI of approximately ~6.1, as opposed to the expected pI value of ~9.6. Without wishing to be bound by theory, this shift in pI may be attributed to the focusing of a protein heterocomplex which includes cytochrome c and may be denatured by SDS. FIG. 14B shows cytochrome c focusing typically at the high end of a 3-10 pH gradient in the presence of 4M urea as well as 0.45% NP-40, a surfactant. The presence the surfactant caused cytochrome c to focus strongly at a high pH, consistent with its high isoelectric point, indicating that the surfactant may participate in a protein complex that has a slightly acidic pI. The proteins were concentrated and collected from whole cell lysate at 111 nL/s (14 s of focusing) at ~300V/cm.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A device for separating a mixture of species, comprising:
   a channel constructed and arranged to receive a fluid flow, the channel comprising substantially non-parallel sidewalls, wherein a first portion of the channel has a channel width that is less than the channel width of a second portion of the channel; and
   at least two electrodes positioned on opposing, external sides of the channel and arranged to form an electric field substantially perpendicular to the primary direction of fluid flow;
   wherein, upon application of an electric field, the device is capable of establishing a pH gradient in a gradient orientation that is perpendicular to the primary direction of fluid flow.

2. A device as in claim 1, wherein, upon application of an electric field, the pH gradient in the first region is essentially identical to the pH gradient in the second region.

3. A device as in claim 1, wherein, upon application of an electric field, the pH gradient in the first region is different than the pH gradient in the second region.

4. A device as in claim 1, wherein the channel comprises a first material having a pH less than 7 and a second material having a pH greater than 7, wherein the first and second materials are positioned on opposing sides of the channel and at least partially define the channel, and wherein each of the first and second materials is in electrical communication with an electrode.

5. A device as in claim 4, wherein the first and second materials comprise a gel.

6. A device as in claim 5, wherein the gel comprises a polymeric material, the polymeric material comprising ionic functional groups covalently bonded to the polymeric material.

7. A device as in claim 6, wherein the polymeric material comprises polyacrylamide.

8. A device as in claim 4, wherein the first material comprises a polymeric material comprising a cationic species covalently bonded to the polymeric material, and the second material comprises a polymeric material comprising an anionic species covalently bonded to the polymeric material.

9. A device as in claim 1, wherein the electrode comprises a metal, metal oxide, metal nitride, carbon, or polymer.

10. A device as in claim 1, wherein the electrode comprises a platinum.

11. A device as in claim 1, wherein the pH gradient has a pH range between 1.0 and 14.0.

12. A device as in claim 1, wherein the pH gradient has a pH range between 3.0 and 10.0.

13. A device as in claim 1, wherein the pH gradient has a pH range between 3.6 and 9.3.

14. A device for separating a mixture of species, comprising:
    a first region comprising a first channel having a channel width, the channel constructed and arranged to receive a fluid flow, and at least two electrodes positioned on opposing, external sides of the first channel and arranged to form an electric field substantially perpendicular to the primary direction of fluid flow; and
    a second region comprising at least two channels fluidly connected to the first channel, the at least two channels constructed and arranged to receive fluid flow from the first channel, and at least two electrodes positioned on opposing, external sides of each of the at least two channels and arranged to form an electric field substantially perpendicular to the primary direction of fluid flow,
    wherein, upon application of an electric field, the device is capable of establishing a pH gradient in a gradient orientation that is perpendicular to the primary direction of fluid flow.

15. A device as in claim 14, wherein, upon application of an electric field, the pH gradient in the first region is essentially identical to the pH gradient in the second region.

16. A device as in claim 14, wherein, upon application of an electric field, the pH gradient in the first region is different than the pH gradient in the second region.

17. A device as in claim 14, wherein the pH gradient in the first region has a pH range different than a pH range of the pH gradient in the second region.

18. A device as in claim 14, wherein the pH gradient in the first region has a rate of change in pH unit per mm in the gradient orientation different than a rate of change in pH unit per mm in the second region in the gradient orientation.

19. A device as in claim 14, wherein each of the first channel and the at least two channels comprises a first material having a pH less than 7 and a second material having a pH greater than 7, wherein the first and second materials are positioned on opposing sides of the channel and at least partially define the channel, and wherein each of the first and second materials is in electrical communication with an electrode.

20. A device as in claim 19, wherein the first and second materials comprises a gel.

21. A device as in claim 20, wherein the gel comprises a polymeric material, the polymeric material comprising ionic functional groups covalently bonded to the polymeric material.

22. A device as in claim 21, wherein the polymeric material comprises polyacrylamide.

23. A device as in claim 19, wherein the first material comprises a polymeric material comprising a cationic species covalently bonded to the polymeric material, and the second material comprises a polymeric material comprising an anionic species covalently bonded to the polymeric material.

24. A device as in claim 14, wherein the electrode comprises a metal, metal oxide, metal nitride, carbon, or polymer.

25. A device as in claim 14, wherein the electrode comprises platinum.

26. A method for separating a mixture of species, comprising:
providing a device comprising at least one channel having a channel width and a fluid flowing through the channel, the channel comprising a first region and a second region, wherein the first region has a first pH gradient across the channel in a gradient orientation that is perpendicular to the primary direction of fluid flow and the second region has a second pH gradient across the channel in the gradient orientation, wherein the first pH gradient is different from the second pH gradient;
exposing a fluid sample comprising a mixture of species to the first region such that the fluid sample is affected by the first pH gradient; and
exposing at least a portion of the fluid sample to the second region such that the fluid sample is affected by the second pH gradient, thereby separating the mixture of species.

27. A method as in claim 26, wherein the first pH gradient has a pH range different than a pH range of the second pH gradient.

28. A method as in claim 26, wherein the first pH gradient has a rate of change in pH unit per mm in the gradient orientation different than a rate of change in pH unit per mm in the gradient orientation.

29. A method as in claim 26, wherein the mixture of species comprises a biological molecule.

30. A method as in claim 26, wherein the mixture of species comprises a protein.

31. A method as in claim 26, wherein the mixture of species comprises a colloid.

32. A method as in claim 26, wherein the mixture of species comprises particles having an average particle size from 2 nm to 100 microns.

33. A method as in claim 26, wherein the fluid sample is at least 10 microliters.

34. A method as in claim 26, wherein the fluid sample is at least 50 microliters.

35. A method as in claim 26, wherein the fluid sample is at least 100 microliters.

36. A method as in claim 26, wherein the fluid sample is at least 250 microliters.

37. A method as in claim 26, wherein the fluid sample is at least 500 microliters.

* * * * *